United States Patent
Feng et al.

(12)

(10) Patent No.: US 6,297,360 B1
(45) Date of Patent: Oct. 2, 2001

(54) AMPHIPATHIC PROTEIN-1

(75) Inventors: Teng-yung Feng; Hae-jan Lin, both of Taipei (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 09/390,598

(22) Filed: Sep. 3, 1999

Related U.S. Application Data

(62) Division of application No. 09/049,577, filed on Mar. 27, 1998, now Pat. No. 5,968,804.

(51) Int. Cl.⁷ .................................................. C07K 14/415

(52) U.S. Cl. .......................... 530/379; 530/350; 530/300; 530/324; 530/370; 435/69.1

(58) Field of Search ..................................... 530/350, 370, 530/379, 300, 324; 435/69.1

(56) References Cited

PUBLICATIONS

Zhong et al., "Design and Synthesis of Amphipathic Antimicrobial Peptides", Int. J. Pept. Protein Res. 45(4):337–347, 1995.

Broekaert et al., "Plant Defensins: Novel Antimicrobial Peptides as Components of the Host Defense System", Plant Physiology 108(4):1353–1358, Aug. 1995.

Terras et al., "Small Cystein–rich Antifungal Proteins from Radish: Their Role in Host Defense", The Plant Cell 7(5):573–588, May 1995.

Powell et al., "Synthetic Antimicrobial Peptide Design", Mol. Plant–Microbe Interact 8(5):792–794, 1995.

*Primary Examiner*—Christoper S. F. Low
*Assistant Examiner*—Gabriele E. Bugaisky
(74) *Attorney, Agent, or Firm*—Fish & Richardson P.C.

(57) ABSTRACT

This invention relates to amphipathic protein-1 polypeptides that can protect plants from tissue damage caused by the hypersensitive response, which is often elicited by bacterial infection in higher plants.

4 Claims, No Drawings

```
                              SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 294 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO:1:

ATGGCTTCAT ACAAAGTGAA ACTTATCACA CCTGACGGAC CAATAGAATT TGATTGCCCA     60

GATAATGTGT ACATTCTTGA TCAAGCTGAG GAAGCAGGAC ATGATCTTCC TTATTCGTGC    120

AGGGCAGGTT CTTGCTCATC TTGTGCTGGT AAAATTGCTG GTGGAGCTGT TGATCAAACT    180

GATGGCAACT TTCTTGATGA TGACCAATTA GAGGAGGGAT GGGTGCTAAC TTGTGTTGCT    240

TATCCACAGT CTGATGTTAC TATTGAGACT CACAAAGAGG CAGAACTCGT GGGC          294

(2) INFORMATION FOR SEQ ID NO:2:

(i) SEQUENCE CHARACTERISTICS:
          (A) LENGTH: 144 amino acids
          (B) TYPE: amino acid
          (D) TOPOLOGY: linear (ii) MOLECULE TYPE: protein (xi) SEQUENCE DESCRIPTION: SEQ ID NO:2:

Met Ala Ser Val Ser Ala Thr Met Ile Ser Thr Ser Phe Met Pro Arg
  1               5                  10                  15

Lys Pro Ala Val Thr Ser Leu Lys Pro Ile Pro Asn Val Gly Glu Ala
             20                  25                  30

Leu Phe Gly Leu Lys Ser Ala Asn Gly Gly Lys Val Thr Cys Met Ala
         35                  40                  45

Ser Tyr Lys Val Lys Leu Ile Thr Pro Asp Gly Pro Ile Glu Phe Asp
```

```
                50                   55                   60
Cys Pro Asp Asn Val Tyr Ile Leu Asp Gln Ala Glu Glu Ala Gly His
 65                  70                  75                  80

Asp Leu Pro Tyr Ser Cys Arg Ala Gly Ser Cys Ser Ser Cys Ala Gly
                    85                  90                  95

Lys Ile Ala Gly Gly Ala Val Asp Gln Thr Asp Gly Asn Phe Leu Asp
                100                 105                 110

Asp Gln Leu Glu Glu Gly Trp Val Leu Thr Cys Val Ala Tyr Pro
        115                 120                 125

Gln Ser Asp Val Thr Ile Glu Thr His Lys Glu Ala Glu Leu Val Gly
        130                 135                 140
```

(2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:3:

```
Ala Glu Tyr Lys Val Thr Leu Leu Asp Pro Gly Gly Ala Gln Gln
 1               5                  10                  15
```

(2) INFORMATION FOR SEQ ID NO:4:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:4:

```
Ala Thr Tyr Lys Val Lys Leu Val Thr Pro Asp Gly Pro Val Glu
 1               5                  10                  15
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:5:

```
Ala Thr Tyr Lys Val Lys Leu Ile Thr Pro Glu Gly Pro Phe Phe
 1               5                  10                  15
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: primer, degenerate (ix) FEATURE:
        (A) NAME/KEY: synthetic oligonucleotide
        (B) LOCATION: 3, 6, and 15
        (D) OTHER INFORMATION: where N at positions 3, 6, and 15 is
            inosine -continued (xi) SEQUENCE DESCRIPTION: SEQ ID NO:6:

GCNACNTAYA ARGTNAAR                                              18

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: primer, degenerate (ix) FEATURE:
        (A) NAME/KEY: synthetic oligonucleotide
        (B) LOCATION: 3, 6, and 12
        (D) OTHER INFORMATION: where N at positions 3, 6, and 12 is
            inosine (xi) SEQUENCE DESCRIPTION: SEQ ID NO:7:

ACNCCNGAYG GNCC                                                  14

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:8:

CATCTTGGTC AAAGTTTGAA TC                                         22

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:9:

AATAGAATTT GATTGCCCAG A                                          21

AMPHIPATHIC PROTEIN-1

CROSS REFERENECE TO RELATED APPLICATIONS

This application is a divisional of application Ser. No. 09/049,577, filed Mar. 27, 1998, now U.S. Pat. No. 5,968,804.

BACKGROUND OF THE INVENTION

The hypersensitive response (HR) of higher plants is characterized by the rapid, localized death of plant cells at the site of pathogen invasion. HR occurs during incompatible pathogen/host interactions, such as when a microorganism that normally causes a disease in its host plant infects a non-host plant. The response is associated with resistance against a variety of pathogens, including nematodes, fungi, viruses, and bacteria. For a review of the hypersensitive response, see Dixon et al., Annu Rev Phytopathol 32:479 (1994) and Godiard et al., Curr Opin Genet Dev 4:662 (1994).

The ability of phytopathogenic bacteria to cause HR in resistant or non-host plants is controlled by a cluster of highly conserved bacterial genes named hypersensitive response and pathogenicity (hrp) genes. Most hrp genes are involved in forming a protein secretion apparatus for harpins, heat-stable and proteinaceous proteins which elicit HR when infiltrated into the leaf intercellular spaces of non-host plants. It is known that, when added to a plant cell culture, harpins induce the exchange of $H^+$ and $K^+$ across the plasmalemma to generate active oxygen species (Baker et al., Plant Physiol 102:1341 [1993]).

SUMMMARY OF THE INVENTION

This invention relates to an isolated nucleic acid encoding an amphipathic protein-1 (AP-1) which decreases the extent or duration of HR in a plant. The term "amphipathic protein-1" refers to any natural or man-made variant of AP-1. For example, the nucleic acid can have the sequence of SEQ ID NO:1 (shown below), have a sequence which hybridizes under stringent conditions to SEQ ID NO:1, or have a sequence which encodes SEQ ID NO:2.

A vector and transformed host cell containing such a nucleic acid is included within the scope of this invention. A vector is any nucleic acid molecule or virus containing regulatory elements or reporter genes for the purpose of, but not limited to, expression in prokaryotic or eukaryotic cells or organisms. A transformed host cell is a host cell into which (or into an ancestor of which) has been introduced, by means of molecular biological techniques, a nucleic acid encoding an AP-1 of this invention. After introduction into the cell, this nucleic acid can exist extrachromosomally or become integrated into the host genome.

The present invention also relates to a substantially pure AP-1, such as SEQ ID NO:2 (shown below) or a protein which differs from SEQ ID NO:2 by at least one conservative amino acid substitution.

A "nucleic acid" encompasses both RNA and DNA, including cDNA, genomic DNA, and synthetic (e.g., chemically synthesized or modified) DNA. The nucleic acid may be double-stranded or single-stranded. Where single stranded, the nucleic acid may be a sense strand or an antisense strand. An "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

By "hybridizes under stringent conditions" is meant the conditions in which a nucleic acid forms a stable, sequence-specific, non-covalent bond with the nucleic acid of SEQ ID NO:1 in solution or on solid support under the low salt and high temperature conditions regarded as stringent and set forth in Sambrook et al (Molecular Cloning, A Laboratory Manual, Sambrook, J., Fritsch, E. F., and Maniatis, T., 2nd ed. [1989] Cold Spring Harbor Laboratory Press). For example, reference nucleic acids such as SEQ ID NO:1 can be immobilized on nitrocellulose filters. Any nucleic acids specifically and non-covalently binding to the immobilized reference nucleic acids in the presence of 0.2×SSC (1.75 g/l NaCl, 0.88 g/l $Na_3$citrate.$2H_2O$; pH 7.0) and 0.1% (w/v) sodium dodecylsulfate at 68° C. are considered to be hybridized under stringent conditions.

The term "substantially pure" as used herein in reference to a given AP-1 polypeptide means that the polypeptide is substantially free from other compounds, such as those in cellular material, viral material, or culture medium, with which the polypeptide may have been associated (e.g., in the course of production by recombinant DNA techniques or before purification from a natural biological source). Polypeptides are substantially free from other compounds when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a polypeptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably at least 100 nucleotides (e.g., 150, 200, 250, or 300 nucleotides).

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. For example, a 10 amino acid polypeptide is said to be at least 80% conserved if it differs from a reference polypeptide by no more than two non-conservative substitutions. An AP-1 polypeptide of this invention is preferably 70% conserved, more preferably 80% conserved, and most preferably 90% conserved as compared to SEQ ID NO:2.

Sequence identity can be measured using sequence analysis software, e.g., the Sequence Analysis Software Package of the Genetics Computer Group, University of Wisconsin Biotechnology Center, 1710 University Avenue, Madison, Wis. 53705 with the default parameters as specified therein.

The BLAST programs, provided as a service by the National Center for Biotechnology Information, are useful for making sequence comparisons. The programs are described in detail by Karlin et al., Proc Natl Acad Sci USA 87:2264 (1990) and 90:5873 (1993), and Altschul et al., Nucl Acids Res 25:3389 (1997) and are available on the Internet.

The isolation and characterization of an AP-1 gene of the invention will allow the production of variant forms of AP-1 polypeptides which may have advantageous activities such as greater HR-blocking activity or greater protein stability.

Other features or advantages of the present invention will be apparent from the following drawings and detailed description of several embodiments, and also from the claims.

DETAILED DESCRIPTION OF THE INVENTION

The invention relates to amphipathic protein-1, a polypeptide which decreases the extent or duration of HR in plants, e.g., in response to a harpin secreted from a bacterium.

Contemplated within the scope of this invention are recombinant nucleic acids or viruses which allow production of AP-1 in a transformed cell or transgenic organism or allow ease of producing specific or non-specific mutations within the AP-1 reading frame. These recombinant nucleic acids or viruses may further include any one of a variety of sequences upstream of the AP-1 coding sequences, such as strong constitutive promoters; within the AP-1 coding sequence, such as introns containing cis-elements that allow high level expression; or downstream of the AP-1 coding sequence, such as efficient polyadenylation signals. The invention further includes any cells containing or producing such nucleic acids or viruses, and any AP-1 polypeptides produced from such cells.

Without further elaboration, it is believed that one skilled in the art can, based on the above disclosure and the isolation of AP-1 polypeptides and genes from the description below, utilize the present invention to its fullest extent. The following examples are to be construed as merely illustrative of how one skilled in the art can isolate AP-1 genes and polypeptides from biological sources, and are not limitative of the remainder of the disclosure in any way. Any publications cited in this disclosure are hereby incorporated by reference.

EXAMPLE 1
Isolation of Amphipathic Protein-1

Three plants were used for the extraction of AP-1. Cotton cultivar (*Gossypium hirsutum* L.) was obtained from the Jiangsu Academy of Agricultural Sciences (Nanking, China). Tomato cultivar (*Lycopersicum esculentum*, Moneymaker, CF4) was obtained from Dr. P. J. G. M. De Wit at Agricultural University, Wageningen, The Netherlands and is available as ATCC Nos. 54003 and 54004. Sweet pepper cultivar (*Capsicum annuum*, ECW) was obtained from Dr. C-F. Wang in the Asian Vegetable Research and Developmental Center (AVRDC; Tainan, Taiwan, Republic of China) and is available as AVRDC Accession No. C00165-1.

Healthy leaves from each plant were homogenized in 0.5 M Tris buffer (pH 8.0) in the presence of 1% (w/v) polyvinylpyrrolidone and 1.5% (v/v) n-octanol. The homogenates were filtrated by nylon mesh and centrifuged at 10,000 g for 30 minutes at 4° C. The fatty layer at the top of the centrifuge tubes was collected, resuspended in Tris buffer (0.05 M, pH 7.5) containing 1 mM phenylmethylsulfonylfluoride and gently shaken for at least 1 hour. The amphipathic extracts were obtained from the soluble phase after centrifugation at 10,000 g for 30 minutes at 4° C.

Amphipathic extracts from the three plants were first separated by Sephacryl S-100 gel filtration (Pharmacia Co.) as follows. 6 mg of total protein in a volume of 5 ml were loaded in a 1.5×100 cm column (Bio-Rad) and eluted with Tris buffer (50 mM, pH 7.5) at a flow rate of 0.1 ml/min using the Econo Chromatography system (Bio-Rad). All fractions were tested for their ability to interfere with HR elicitor activity by infiltrating equal amounts of the eluted proteins and harpin$_{Pss}$ into tobacco plant leaves (procedure described below). Fractions 49–51 from all plant sources contained significant HR inhibitory activity. Such fractions were pooled for the next step of purification.

A 1.5×30 cm column (Bio-Rad) containing DEAE Sepharose CL-6B (Pharmacia) was used for further purification. A 0 to 1.0 M NaCl gradient in Tris buffer (50 mM, pH 7.5) was used to elute proteins at a flow rate of 0.5 ml/min, using the Econo Chromatography System. The eluents were desalted using a Microconcentrator with 10 kDa molecular weight cut-off membrane (Amicon Co.) and washed three times with phosphate buffer. Fractions 26–32 from all plant sources showed significant HR inhibitory activity, which correlated with a single 22 kDa polypeptide as visualized by subjecting the various fractions to sodium dodecylsulfate-polyacrylamide gel electrophoresis (SDS-PAGE) and subsequent silver staining. The 22 kDa protein purified as described above is named amphipathic protein-1 or AP-1.

The AP-1 yield from tomato leaves was about $10^{-8}$ gram protein/gram leaf. The yield from sweet pepper or cotton was about $10^{-9}$ gram protein/gram leaf.

The N-terminal amino acids of AP-1 from the three plants were determined. AP-1 was isolated, separated by SDS-PAGE, transferred onto PVDF membranes, and analyzed using a ABI 476A protein sequencer (Applied biosystems, Inc.) as instructed by the manufacturer. The first 15 amino acids of each AP-1 from the three plants were determined as follows:

| | |
|---|---|
| Cotton: | Ala Glu Tyr Lys Val Thr Leu Leu Asp Pro Gly Gly Ala Gln Gln (SEQ ID NO: 3) |
| Pepper: | Ala Thr Tyr Lys Val Lys Leu Val Thr Pro Asp Gly Pro Val Glu (SEQ ID NO: 4) |
| Tomato: | Ala Thr Tyr Lys Val Lys Leu Ile Thr Pro Glu Gly Pro Phe Phe (SEQ ID NO: 5) |

EXAMPLE 2

AP-1 Delays Harpin-Induced Hypersensitive Response

To test the effect of AP-1 on Harpin induced HR, Harpin$_{Pss}$ (harpin from *Pseudomonas syringae* pv. *syringae*)

protein was first prepared. Harpinp$_{Pss}$ protein was extracted by the methods described in He et al., Cell 73:1255 (1993). E. coli DH5α (pSYH10) containing the harpin$_{Pss}$ gene was grown in Lauria Broth containing ampicillin (50 μg/ml) at 37° C. in the dark and shaken overnight in the presence of isopropyl-β-D-thiogalactoside (IPTG). To obtain harpin$_{Pss}$ the bacteria were washed, sonicated for 30 seconds, and boiled for 10 minutes. After boiling, the extracts were centrifuged at 10,000 g for 10 minutes. Supernatants were desalted by Microconcentrators (Amicon) and were stored at 4° C.

The HR assay was performed as described in Huang et al., J Bacteriol 170:4748 (1988). Fully expanded tobacco leaves (Nicotiana tabacum L. cv. Xanthi, available as ATCC Nos. 54037 and 54039) were wounded with a 25 gauge needle to form tiny holes on the lower surfaces of the leaves. Harpin$_{Pss}$ or bacterial cells was infiltrated by pressing a 1 ml blunt syringe through the hole. The infiltrated plant was incubated in a 28° C., 12 hour light/12 hour dark incubator. The HR was recorded by photography.

Various amounts of purified AP-1 were mixed with 10 μg of harpin$_{Pss}$, and the resulting mixture was infiltrated into the intercellular spaces of tobacco leaves. The area of necrosis 20 hours after infiltration in the presence of as little as 50 ng of tomato AP-1 was reduced in comparison with the absence of AP-1.

AP-1 also caused a significant postponement of HR-like necrosis induced by harpin$_{Pss}$-harboring bacteria. Bacteria was infiltrated in the absence or presence of 500 ng of tomato AP-1 into the intercellular spaces of the tobacco leaf at the equivalent of 5×10$^6$ CFU/ml. At six days post-inoculation, the bacteria caused significant necrosis in the absence of AP-1. In the presence of AP-1, the infiltrated plant tissue was relatively healthy.

The HR reduction rate was approximately proportional to the dosage of AP-1 in the range from 50 ng to 500 ng and approached 80% reduction of HR at the highest dose at 20 hours post-inoculation. 250 ng of AP-1, which corresponds to a harpin$_{Pss}$ to AP-1 molar ration of 40 to 1, established about a 50% reduction of the HR-necrosis area.

A time-course of AP-1 infiltration was performed with respect to P. syringae inoculation. HR was not delayed when AP-1 was infiltrated 30 or 60 minutes prior to inoculation. In contrast, AP-1 delayed HR significantly when AP-1 and bacteria were infiltrated simultaneously.

EXAMPLE 3

AP-1 Suppresses Bacterial Growth

P. syringae pv. syringae was infiltrated, along with tomato AP-1, into the intercellular spaces of tobacco leaves. The bacteria population was monitored as described in Li et al., J Bacteriol 174:1742 (1992). 1×10$^7$ cfu/ml of log-phase growth bacteria was used for each inoculation. Leaf disks (0.5 cm diameter) punched around the infiltration holes were homogenized in 100 μl phosphate buffer (0.01 M, pH 6.5) and diluted up to 10,000 fold. 100 μl of bacteria were plated on 9 cm LB agar plates, and the colonies counted after overnight growth. Each dilution was plated in triplicate.

Within 48 hours post-inoculation, the population of the bacteria and the bacteria treated with 1 μg of bovine serum albumin (BSA) steadily increased from 10$^5$ CFU/ml to 10$^7$ CFU/ml per leaf disk. However, in the presence of 1 μg of AP-1, the bacterial population was reduced from an initial 5×10$^5$ CFU/ml to 5×10$^4$ CFU/ml 16 hours post-inoculation.

EXAMPLE 4

Cloning of an AP-1 cDNA

Total RNA was isolated from pepper leaves (Capsicum annuum) as described in Nelson, "Preparation of DNA and RNA from leaves: expanded blades and separated bundle sheath and mesophyll cells" In The Maize Handbook, Freeling et al. editors, pp. 541–545, Springer-Verlag, NY, 1994. Two grams of pepper leaves were homogenized, using a Pro 200 homogenizer, in 10 ml of extraction buffer (0.1 M TRIS-HCl, pH 8.5, 0.1 M NaCl, 20 mM EDTA, and 1% lauroyl sarcosine). RNA was separated from DNA by precipitation with 2 M LiCl. First-strand cDNA synthesized using an oligo (dT) primer and Superscript Reverse Transcriptase (GibcoBRL/Life) according to the manufacturer's instructions.

For PCR, 2 μl of RT mixture was combined with 0.6 μM of modified degenerate primer (5'-GCiACiTAYAARGTiAAR-3'; [SEQ ID NO:6]), 0.2 μM of 5'-(dT)N anchor primer, 1 mM dNTP, and 2.5 units of Taq DNA polymerase (GibcoBRL/Life). The sequence of PCR primers used to clone AP-1 were derived from the N-terminal amino acid sequence as described in Example 1 above. The amplification cycle parameters were as follows: 5 minutes at 94° C.; two cycles of 1 minute at 94° C., 2 minutes at 45° C., 1.5 minutes at 72° C.; 38 cycles of 45 seconds at 94° C., 2 minutes at 63° C., 1 minute at 72° C.; and 10 minutes at 72° C. PCR products were purified using a spin-column with a silica-gel binding membrane (Qiagen).

The second, nested PCR was amplified by mixing together 1 μl of the above purified PCR products, 0.4 μM of modified degenerate primer (5'-ACiCCiGAYGGiCC-3'; SEQ ID NO:7), 0.4 μM of 3' oligo 5' (dT)$_{18}$N anchor primer and otherwise treated as indicated immediately above.

RT-PCR products were run on an agarose gel and eluted using a Qiaquick gel extraction kit (Qiagen). The purified CDNA fragments were treated with polynucleotide kinase and ligated into the pT7Blue blunt-end vector (Novagen) according to manufacturer's instructions.

The sequence of cDNA inserts was determined by the dideoxy chain termination method using a Sequenase kit (PE-ABI) and an ABI nucleic acid sequencer.

To amplify the 5' Cap region of the gene, first-strand cDNA was synthesized by performing RT-PCR (GibcoBRL/Life) in the presence of 0.5 μM Capswitch primer (Clontech) and 800 ng pepper mRNA. mRNA was isolated from total pepper RNA using oligo (dT) affinity magnetic particles (Straight-A MRNA Isolation System, Novagen). PCR amplification of the 5' cap region was performed in a 30 μl volume containing 2 μl single-strand cDNA, the 5' Capswitch primer, and 3'-specific primer (5'-CATCTTGGTCAAAGTTTGAATC-3'; SEQ ID NO:8) corresponding to the 3' noncoding region of the AP-1 clone. Amplification was performed using the following parameters: 35 cycles of 94° C. for 45 seconds, 53° C. for 1 minute, and 72° C. for 1 minute; and 5 minutes at 72° C. Following PCR amplification, the Klenow cDNA fragments were purified, treated with polynucleotide kinase, and ligated into pT7Blue Blunt vector (Novagen).

A 785 base pair full-length cDNA clone (pap-1), containing N-terminal deduced amino acid sequences of the putative mature peptide, was isolated. This clone encodes a polypeptide with the same N-terminal amino acids as described in Example 1 above. The pap-1 cDNA clone contains an open reading frame (ORF) of 432 bp, encoding a protein of 144 amino acids, which includes a 47 amino acid putative secretion peptide. The coding sequence of the open reading frame is shown below.

ATGGCTTCATACAAAGTGAAACTTATCA-
CACCTGACGGACCAATAGAATTTGATTGCCCA
GATAATGTGTACATTCTTGATCAAGCT-
GAGGAAGCAGGACATGATCTTCCTTATTCGTGC

AGGGCAGGTTCTTGCTCATCTTGTGCTG-
GTAAAATTGCTGGTGGAGCTGTTGATCAAACT
GATGGCAACTTTCTTGATGATGAC-
CAATTAGAGGAGGGATGGGTGCTAACT-
TGTGTTGCTTATCCACAGTCTGATGT-
TACTATTGAGACTCACAAAGAGGCAGAACTCGTG
GGC (SEQ ID NO:1)

The deduced amino acid sequence contains a 2Fe-2S domain, a myristoylation site, and two phosphorylation sites. The AP-1 amino acid sequence is shown below.

```
Met Ala Ser Val Ser Ala Thr Met Ile Ser Thr Ser  (SEQ ID NO:2)

Phe Met Pro Arg Lys Pro Ala Val Thr Ser Leu Lys

Pro Ile Pro Asn Val Gly Glu Ala Leu Phe Gly Leu

Lys Ser Ala Asn Gly Gly Lys Val Thr Cys Met Ala

Ser Tyr Lys Val Lys Leu Ile Thr Pro Asp Gly Pro

Ile Glu Phe Asp Cys Pro Asp Asn Val Tyr Ile Leu

Asp Gln Ala Glu Glu Ala Gly His Asp Leu Pro Tyr

Ser Cys Arg Ala Gly Ser Cys Ser Ser Cys Ala Gly

Lys Ile Ala Gly Gly Ala Val Asp Gln Thr Asp Gly

Asn Phe Leu Asp Asp Asp Gln Leu Glu Glu Gly Trp

Val Leu Thr Cys Val Ala Tyr Pro Gln Ser Asp Val

Thr Ile Glu Thr His Lys Glu Ala Glu Leu Val Gly
```

To test for the distribution of ap-1 in various plants, genomic DNA was isolated from pepper, tomato, tobacco, cotton, *Arabidopsis thaliana* and Petunia sp. according to Nelson, Id. For PCR detection of ap-1 sequences, a 5' primer in the ap-1 coding sequence (5'-AATAGAATTTGATTGCCCAGA-3'; SEQ ID NO:9) and 3'primer (5'-CATCTTGGTCAAAGTTTGAATC-3'; SEQ ID NO:8) in the 3' untranslated region were used. The 5' primer and the 3' primer was expected to produce a 373 bp PCR product. The PCR was performed in MgCl$_2$ buffer containing 1 mM DNTP, 2.5 units of Taq DNA polymerase, 200 ng genomic DNA and 5% dimethylsulfoxide. The amplification parameters were as follows: 5 minutes at 94° C.; 5 cycles of 1 minute at 94° C., 1 minute at 51° C., and 1 minute at 72° C.; and 30 cycles of 45 seconds at 94° C., 1 minute at 51° C., and 1 minute at 72° C.; and 5 minutes at 72° C.

A 373 bp fragment could be amplified from pepper, tomato, tobacco, Petunia, and cotton genomic DNA but not from Arabidopsis genomic DNA.

EXAMPLE 5

In Vitro Expression of Cloned AP-1

In order to transiently express pepper AP-1 in vivo, the pap1coding region was subcloned into a bamboo mosaic potexvirus satellite (satBaMV) vector, which is described in Lin et al., Proc Natl Acad Sci USA 93:3138 (1996), hereby designated BSAP1. BASP1 was used to in vitro transcribe an RNA containing the 432 bp ap-1 open reading frame and about 400 bp of viral sequence. The BaMV-L and satBaMV vector transcripts were inoculated, along with the ap-1 transcript, into the tobacco *Nicotiana benthamiana*. Northern blot hybridization was used to detect the replication of viral RNA in tobacco. The total RNA extracted 7 days after inoculation was separated on 1% agarose gels, transferred to nylon membranes, and hybridized with a probe specific to the 3' end of satBaMV (+)RNA as described in Lin et al., (1996) Id. The Northern indicated that the BSAP1 RNA was expressed in the tobacco.

For in vitro translation, the satBaMV vector transcripts were translated in rabbit reticulocyte lysate (Promega) in the presence of $^{35}$S-labeled methionine and analyzed by SDS-PAGE. The in vitro translation produced a 27 kDa protein. The size of the translated protein was about two folds larger than the predicted molecular weight of the ap1 encoded polypeptide (14 kDa), including the putative secretion peptide region.

For expression of AP-1 in *E. coli*, the mature polypeptide of the pap1 clone was cloned into the Bam HI and Hind III sites of the pQE-30 vector (Qiagen) and transformed into the bacterial host strain M15. The N-terminal 6× His-tagged proteins were induced with IPTG and purified by Ni-NTA resin Spin Kits (Qiagen). For immunoblot detection of the 6× His-tagged AP-1 polypeptides, the *E. coli* lysate was run on SDS-PAGE gels, transferred onto nitrocellulose membranes, and detected with $^{RGSH}$·His antibodies (Qiagen).

In the above system, the translated protein, which does not include the secretion peptide, was also observed to be double the size (22 kDa) of the predicted molecular weight of AP-1. This size, however, is consistent with the estimated molecular weight of the plant AP-1 polypeptide as described in Example 1 above.

EXAMPLE 6

Cloned AP-1 Delays Harpin$_{Pss}$-mediated HR

To determine the biological activity of cloned AP-1, a mixture of the purified harpin$_{Pss}$ and *E. coli* expressed pepper AP-1, as obtained in Example 5 above, was infiltrated into tobacco leaves as described in Example 2 above. A light yellowing response was induced by harpin$_{Pss}$ within one day post-inoculation and was followed by the formation of harpin$_{Pss}$-induced necrosis two days post-inoculation. The necrosis area was reduced more than 50% two days post-inoculation when 200 ng AP-1 was co-inoculated with the harpin.

EXAMPLE 7
Cloned AP-1 Suppresses HR induced by *Erwinia carotovora* subsp. *carotovora*

Fifty microliters containing different concentrations of the pathogenic bacteria *Erwinia carotovora* subsp. *carotovora* in the presence or absence of 0.15 µM AP-1 were inoculated into tobacco leaves and assayed for HR inhibition as described in Example 2 above. *E. carotovora* subsp. *carotovora* can be obtained as ATCC No. 12312.

AP-1 protected the plant tissue from *E. carotovora*-induced HR necrosis at one day post-inoculation for bacterial concentrations up to $10^7$ CFU/ml.

EXAMPLE 8
Agrobacterium-Mediated Overexpression of AP-1 Suppresses HR Induced by *Xanthomonas campestris* pv. *vesicatoria*

Agrobacterium-mediated transient overexpression of sweep pepper AP-1 was established in sweet pepper plants as described in Van den Ackerveken et al., Cell 87:1307 (1996). Agrobacterium bacteria was infiltrated into fully expanded leaves of the sweet pepper overexpressing AP-1. Plants were kept for two days at 20° C., 16 hour light/8 hour dark, 100% humidity and then moved to 28° C., 16 hour light/8 hour dark, 80% humidity. Fifty microliters of *Xanthomonas campestris* pv. *vesicatoria* suspension at $1\times10^4$ CFU/ml was inoculated eight days after the Agrobacterium inoculation in the same region and incubated for 24 hours. *X. campestris* pv. *vesicatoria* can be obtained as ATCC Nos. 11551 and 11633.

The Agrobacterium-mediated expression of AP-1 prevented HR necrosis induced by the pathogenic *X. campestris*.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A substantially pure amphipathic polypeptide encoded by a nucleic acid hybridizing to the compliment of a reference nucleic acid consisting of SEQ ID NO:1, wherein the hybridization is performed in the presence of 0.2× SSC and 0.1% (w/v) sodium dodecylsulfate and at 68° C.

2. The polypeptide of claim 1, wherein the polypeptide decreases the growth of a bacterium in a plant.

3. The polypeptide of claim 1, wherein the polypeptide is derived from a cotton, pepper, tobacco, or tomato plant.

4. The polypeptide of claim 1, wherein the polypeptide comprises SEQ ID NO:2.

* * * * *